US006225269B1

(12) United States Patent
Baker

(10) Patent No.: US 6,225,269 B1
(45) Date of Patent: May 1, 2001

(54) NAIL POLISH REMOVER

(76) Inventor: Bradley M. Baker, 706 Birmingham La., Monroe, NC (US) 28110

( * ) Notice: Subject to any disclaimer, the term of this patent is extended or adjusted under 35 U.S.C. 154(b) by 0 days.

(21) Appl. No.: 09/643,561

(22) Filed: Aug. 22, 2000

(51) Int. Cl.$^7$ .............................. C11D 7/50; A61K 7/047
(52) U.S. Cl. ......................... 510/118; 510/405; 510/407; 510/437; 510/403
(58) Field of Search .................................. 510/118, 403, 510/405, 407, 437

(56) References Cited

U.S. PATENT DOCUMENTS

| | | | |
|---|---|---|---|
| 3,928,561 | * 12/1975 | Baldwin | ................................. 424/61 |
| 4,085,059 | 4/1978 | Smith et al. . | |
| 4,530,726 | 7/1985 | Montiel . | |
| 4,605,670 | 8/1986 | Saito et al. . | |
| 4,804,486 | 2/1989 | Day . | |
| 4,824,662 | 4/1989 | Hofmann . | |
| 4,954,621 | 9/1990 | Masaoka et al. . | |
| 5,011,621 | 4/1991 | Sullivan . | |
| 5,024,779 | 6/1991 | Helioff et al. . | |
| 5,024,780 | 6/1991 | Leys . | |
| 5,077,038 | 12/1991 | Hofmann . | |
| 5,098,591 | 3/1992 | Stevens . | |
| 5,143,639 | 9/1992 | Krawack . | |
| 5,173,288 | 12/1992 | Everhart et al. . | |
| 5,310,496 | 5/1994 | Taylor . | |
| 5,342,536 | 8/1994 | Miner et al. . | |
| 5,346,640 | 9/1994 | Leys . | |
| 5,346,652 | 9/1994 | Dotolo et al. . | |
| 5,372,742 | 12/1994 | Bayless . | |
| 5,413,795 | 5/1995 | Lee et al. . | |
| 5,427,710 | 6/1995 | Stevens . | |
| 5,464,555 | 11/1995 | Bayless . | |
| 5,468,417 | 11/1995 | LeGrow . | |
| 5,486,305 | 1/1996 | Faryniarz et al. . | |
| 5,494,611 | 2/1996 | Howe . | |
| 5,985,816 | * 11/1999 | Vlasblom | ............................ 510/365 |
| 6,071,865 | * 6/2000 | Pickering et al. | ................... 510/118 |
| 6,090,769 | * 7/2000 | Vlasblom | ............................ 510/365 |
| 6,096,699 | * 8/2000 | Bergemann et al. | ................ 510/201 |

FOREIGN PATENT DOCUMENTS

WO 9003419    4/1990  (WO) .

* cited by examiner

*Primary Examiner*—Lorna M. Douyon

(57) ABSTRACT

A nail polish remover composition comprising aliphatic dibasic esters and alkali refined soybean oil. Preferably, the composition may further include a thickener to make the composition a non-pourable gel. The composition may further include fragrances and color additives for final product aesthetics.

4 Claims, No Drawings

NAIL POLISH REMOVER

BACKGROUND

1. Field of the Invention

The invention relates to nail polish removers and, more particularly, to nail polish removers having good polish dissolving and removal characteristics, skin conditioning properties, low volatility, low flammability, low odor, in addition to being easy to clean up.

2. Background of the Related Art

Finger and toe nail polishes are typically lacquers. Nail polish removal requires a composition that dissolves dried lacquer. Many compositions are known which are useful in removing laquer from fingernails or toenails. These compositions depend upon the solvent action of acetone or other solvents to soften or dissolve the laquer. Acetone is a flammable and toxic substance that rapidly evaporates and emits a characteristic odor. Acetone is also toxic, penetrates skin and can leave a difficult to remove white residue on the cleaned nail. The other solvents used, including but not limited to ethyl acetate, and combinations including ethylene and/or propylene carbonate or diethers and diesters, have certain undesirable effects similar to that of acetone.

Numerous attempts have been made to develop polish removers that avoid the problems of known removers and there is still a need for improved nail polish removers.

An object of the invention is to provide a nail polish remover that has improved polish removal characteristics, skin conditioning properties, low volatility, low flammability, low odor, in addition to being easy to clean up.

A further object of the invention is to provide a nail polish removing composition that is a non-pourable gel.

These and other objects of the invention will become more readily apparent through the detailed description of the invention that follows hereunder.

BRIEF SUMMARY OF THE INVENTION

The invention relates to a nail polish remover composition in which aliphatic dibasic esters and alkali refined soybean oil are mixed to produce a base to which other ingredients including but not limited to thickeners, fragrances and color additives can be added and in which the final composition has improved nail polish removal characteristics, skin conditioning properties, low volatility, low flammability, low odor, in addition to being easy to clean up.

DESCRIPTION

The composition of the present invention is preferably used as a nail polish remover.

The easy to use, easy to make composition is made by mixing generally soybean oil and aliphatic dibasic esters. Fragrances and/or color additives can be added to the nail polish remover composition for product aesthetics. The nail polish remover composition may be further modified by the addition of a thickener to create a non-pourable gel.

Soybean oil has skin conditioning properties that tend to alleviate the drying effect that solvents have on the skin, nail and cuticle of the user. Suitable soybean oils are those derived from alkali refined single or double pressed soybeans having carbon-hydrogen chain lengths in the range of between eight and twenty-two carbon atoms, $C_8$–$C_{22}$.

Aliphatic dibasic ester is a clear, colorless liquid produced from dibasic acids. Suitable aliphatic dibasic esters include mixtures of refined dimethyl esters of adipic acid, glutaric acid, and succinic acid. The suitable aliphatic dibasic esters have strong and selective solvency, good stability, low vapor pressure, low toxicity and relatively non-facile skin penetration. The suitable aliphatic dibasic esters have the following formula: $CH3OOC(CH2)n-COOCH3$, where n=2, 3 and 4. Especially suitable is a mixture of 55–65% dimethyl glutarate, 10–25% dimethyl adipate and 15–25% dimethyl succinate available commercially from E. I. du Pont de Nemours and Company.

Suitable thickeners include hydroxypropyl methylcellulose. Especially suitable is hydroxypropyl methylcellulose available commercially from The DOW Chemical Company.

Suitable color additives, such as FD&C Red #3 Powder No. 07007, may be added to the nail polish remover composition for product aesthetics. FD&C Red #3 Powder No. 07007 is available commercially from Prime Ingredient Systems, Inc. of Saddle Brook, N.J.

Suitable fragrances, such as Odor Modifier #10131.OS Apricot, may be added to the nail polish remover composition for product aesthetics. Odor Modifier #10131.OS Apricot is available commercially from Odor Control Co., Inc. of Scottsdale, Ariz.

The improved nail polish remover composition consists of a mixture, by weight proportion, of between about 70% and about 99% of a mixture of aliphatic dibasic esters, and between about 1% and about 30% alkali refined soybean oil.

In an alternative embodiment, thickener is added to the nail polish remover composition, by weight proportion, in an amount from 0 to about 10%, to produce a non-pourable nail polish remover gel with a kinematic velocity of greater than 50,000 centipoise.

Optionally, there may be color additives added to the nail polish remover composition, by weight proportion, in an amount from 0 to about 1%.

Optionally, there may be fragrances added to the nail polish remover composition, by weight proportion, in an amount from 0 to about 1%.

The nail polish remover composition of the present invention has low flammability, i.e., a flash point of greater than 212 degrees Fahrenheut, an evaporation rate that is between 200 and 1,200 times slower than that of acetone and is only a level 1 fire hazard.

The nail polish remover composition of the present invention is not a hazardous substance under federal environmental law and is not subject to federal toxic release reporting requirements. The composition is also not subject to California's Proposition 65.

One particularly suitable composition is identified below:

| Ingredient | % by Weight | Ranges |
| --- | --- | --- |
| Aliphatic dibasic ester | 92.49% | 70-99% |
| Alkali refined soybean oil | 5.00% | 1-30% |
| Thickener | 1.50% | 0-10% |
| FD&C Red #3 Powder No. 07007 | 0.01% | 0-1% |
| Odor Modifier #10131.OS Apricot | 1.00% | 0-1% |

Although said suitable composition represents a preferred composition, other compositions within the ranges set out above can be used.

What is claimed is:

1. A nail polish remover composition comprising: (i) from about 1% to about 30% by weight of soybean oil; and (ii) from about 70% to about 99% by weight of aliphatic dibasic esters.

2. A composition according to claim 1 further comprising from 0 to about 1% by weight of color additive and from 0 to about 1% by weight of fragrance.

3. A composition according to claim 1 further comprising from 0 to about 10% by weight of thickener.

4. A composition according to claim 1 further comprising from 0 to about 10% by weight of thickener, from 0 to about 1% by weight of color additive and from 0 to about 1% by weight of fragrance.

* * * * *